United States Patent [19]
Long

[11] Patent Number: 5,833,689
[45] Date of Patent: Nov. 10, 1998

[54] VERSATILE ELECTROSURGICAL INSTRUMENT CAPABLE OF MULTIPLE SURGICAL FUNCTIONS

[75] Inventor: Gary Long, Cincinnati, Ohio

[73] Assignee: SNJ Company, Inc., Cincinnati, Ohio

[21] Appl. No.: 628,751

[22] Filed: Apr. 4, 1996

Related U.S. Application Data

[63] Continuation-in-part of Ser. No. 329,342, Oct. 26, 1994, Pat. No. 5,556,397.

[51] Int. Cl.$^6$ .................................................. A61B 17/39
[52] U.S. Cl. ................................................ 606/48; 606/50
[58] Field of Search ................................... 606/41, 45–50

[56] References Cited

U.S. PATENT DOCUMENTS

| | | |
|---|---|---|
| 4,538,612 | 9/1985 | Patrick, Jr. . |
| 4,688,569 | 8/1987 | Rabinowitz . |
| 4,706,667 | 11/1987 | Roos . |
| 4,823,791 | 4/1989 | D'Amelio et al. . |
| 5,013,312 | 5/1991 | Parins et al. . |
| 5,089,002 | 2/1992 | Kirwan, Jr. ................................ 606/45 |
| 5,122,137 | 6/1992 | Lennox ..................................... 606/49 |
| 5,234,429 | 8/1993 | Goldhaber . |
| 5,277,696 | 1/1994 | Hagen . |
| 5,281,216 | 1/1994 | Klicek . |
| 5,300,069 | 4/1994 | Hunsberger et al. . |
| 5,330,470 | 7/1994 | Hagen . |
| 5,342,357 | 8/1994 | Nardella . |
| 5,556,397 | 9/1996 | Long et al. ................................ 606/48 |

OTHER PUBLICATIONS

"Safer Electrosurgery" information booklet by NDM, 3040 East River Road, Dayton, Ohio 45401–0154.
Informational product brochure on "Elekrotom BiCut" device by Berchtold AmBh Co., P.O. Box 4052, D–7200 Tuttlingen, Germany.
Instructional Booklet titled "Hazards of Electrosurgery", pp. 1–12, published by Education Design of Denver, CO.
Essentials of Monopolar Electrosurgery for Laparoscopy, by Voyles et al.
"Education and Engineering Solutions for Potential Problems With Laparascopic Monopolar Electrosurgery" by Voyles et al., The American Journal of Surgery, vol. 164, pp. 57–62.

*Primary Examiner*—Michael Peffley
*Attorney, Agent, or Firm*—McDermott, Will & Emery

[57] ABSTRACT

A coaxial electrosurgical instrument has an elongate inner electrode insulated from and contained coaxially within a hollow tubular elongate outer electrode, each electrode having a distal uninsulated end portion contactable simultaneously to tissue. A controlled, high-frequency, potential difference is provided between the electrodes so that an electrical current flows substantially only through contacted tissue which lies between the contacting portions of the inner and outer electrodes. An undamped voltage enables incision of the tissue. Cauterization and coagulation are performed by applying a periodically damped voltage. The outer electrode has an end surface of an uninsulated distal end portion to form a leading edge. An axially oriented cutout extends inwardly from the leading edge and accommodates a distal end portion of the insulating sleeve, permitting selective location of the inner and outer electrode surfaces contacting tissue during use. The inner electrode has an inclined distal end with a smoothly rounded bulbous end which extends forwardly and radially outwardly of the outer electrode. A gentle hooking force can be applied thereby to hold tissue between the electrodes to enable precise surgical operations.

26 Claims, 10 Drawing Sheets

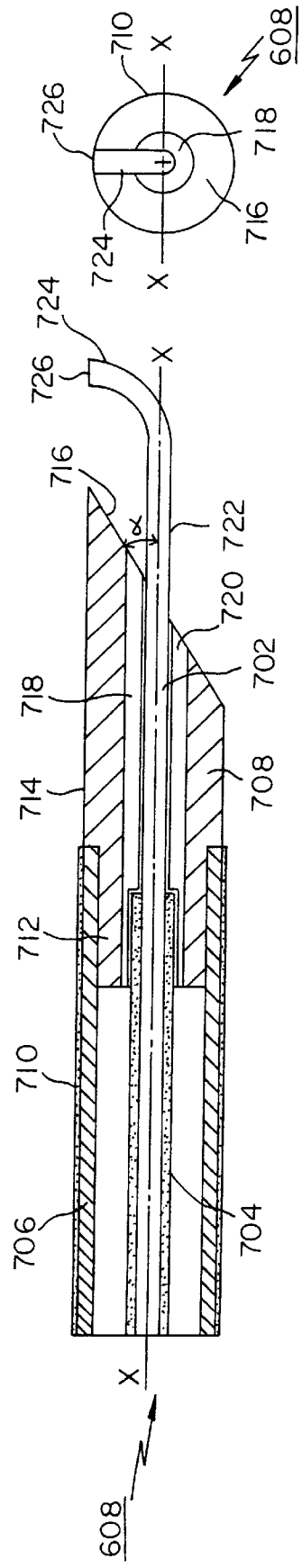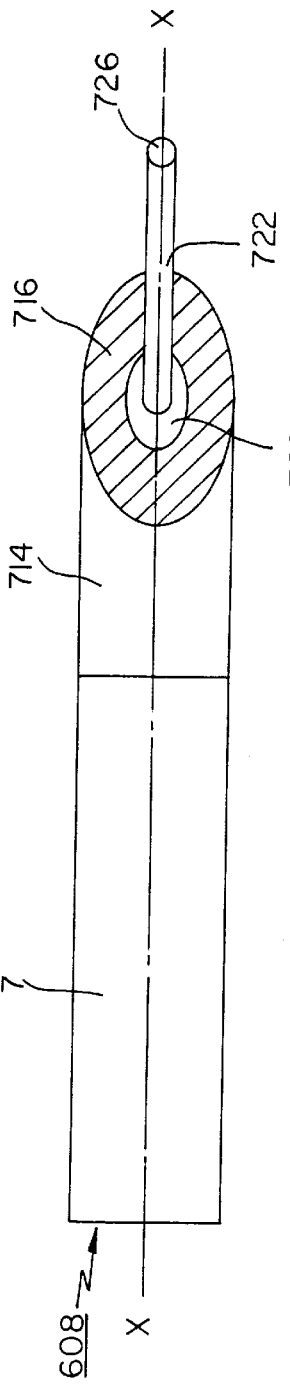
FIG. 7(A)
FIG. 7(B)
FIG. 7(C)

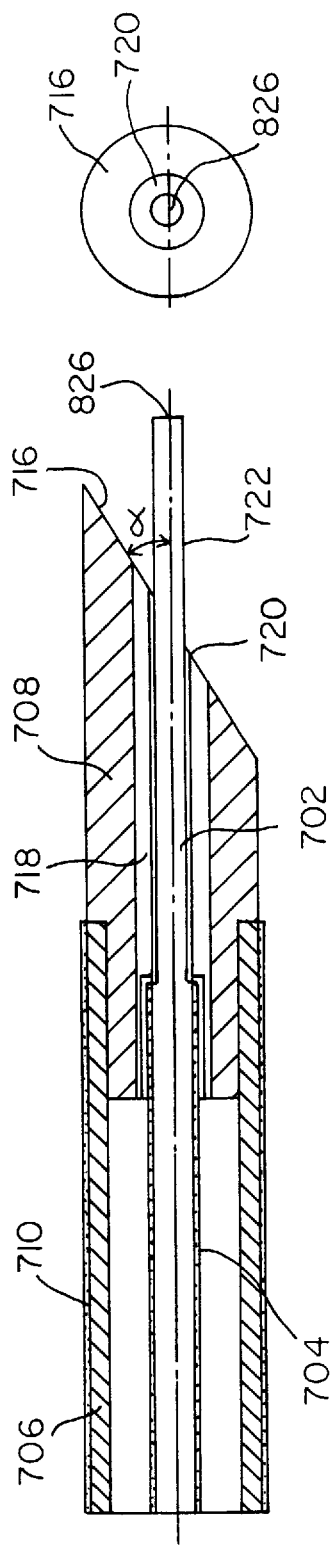
FIG. 8(A)
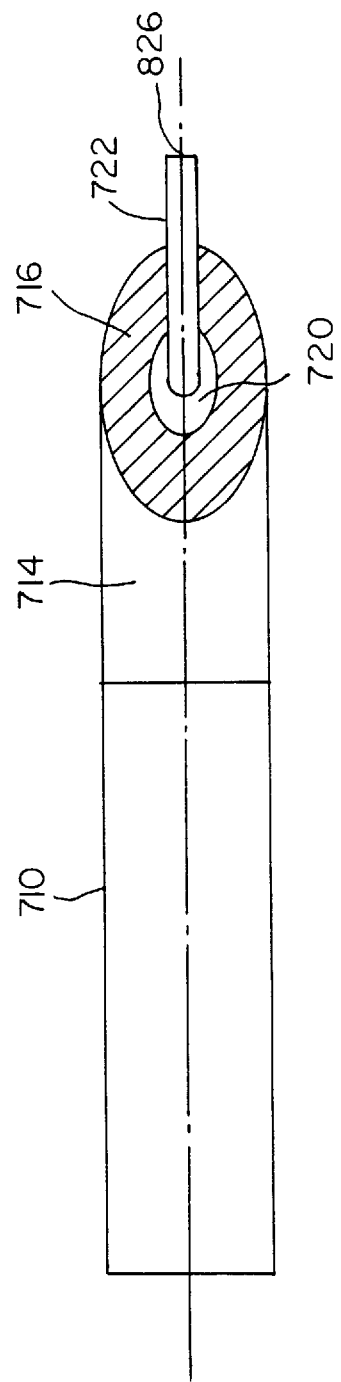
FIG. 8(C)
FIG. 8(B)

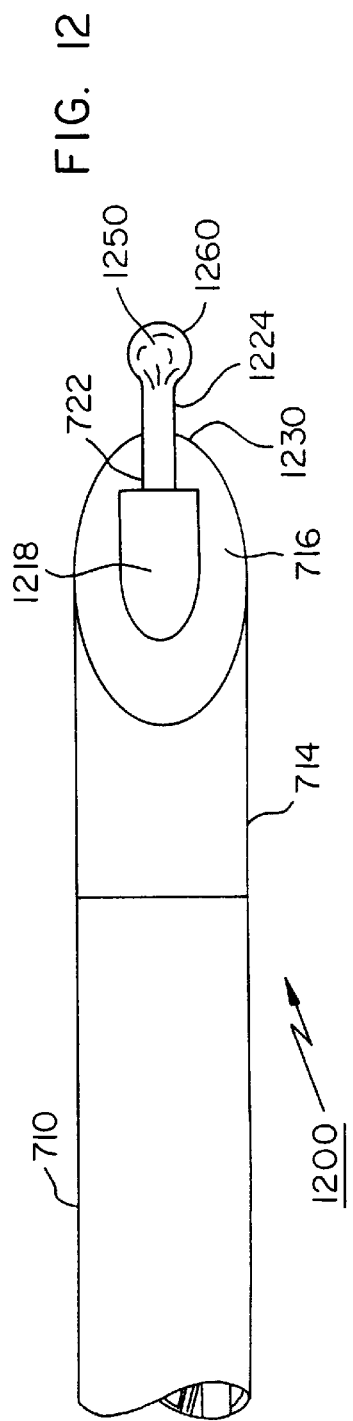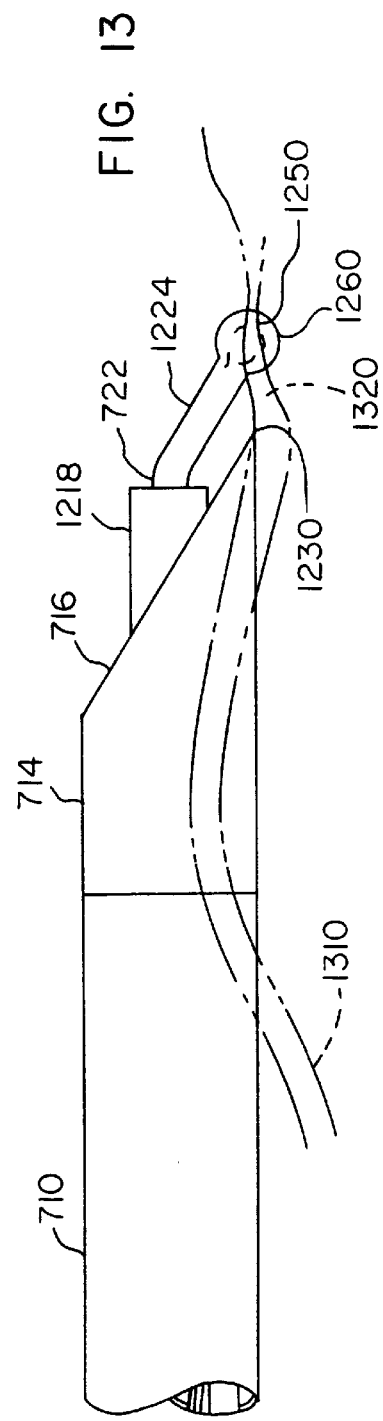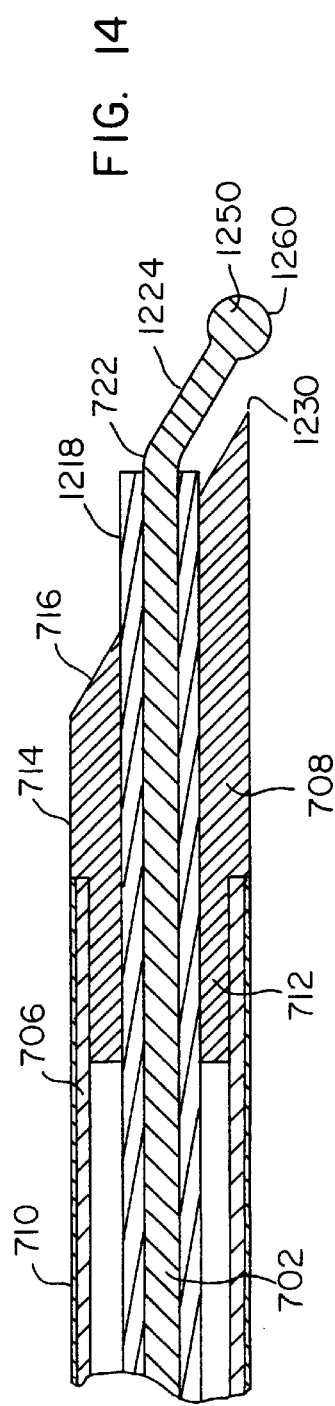

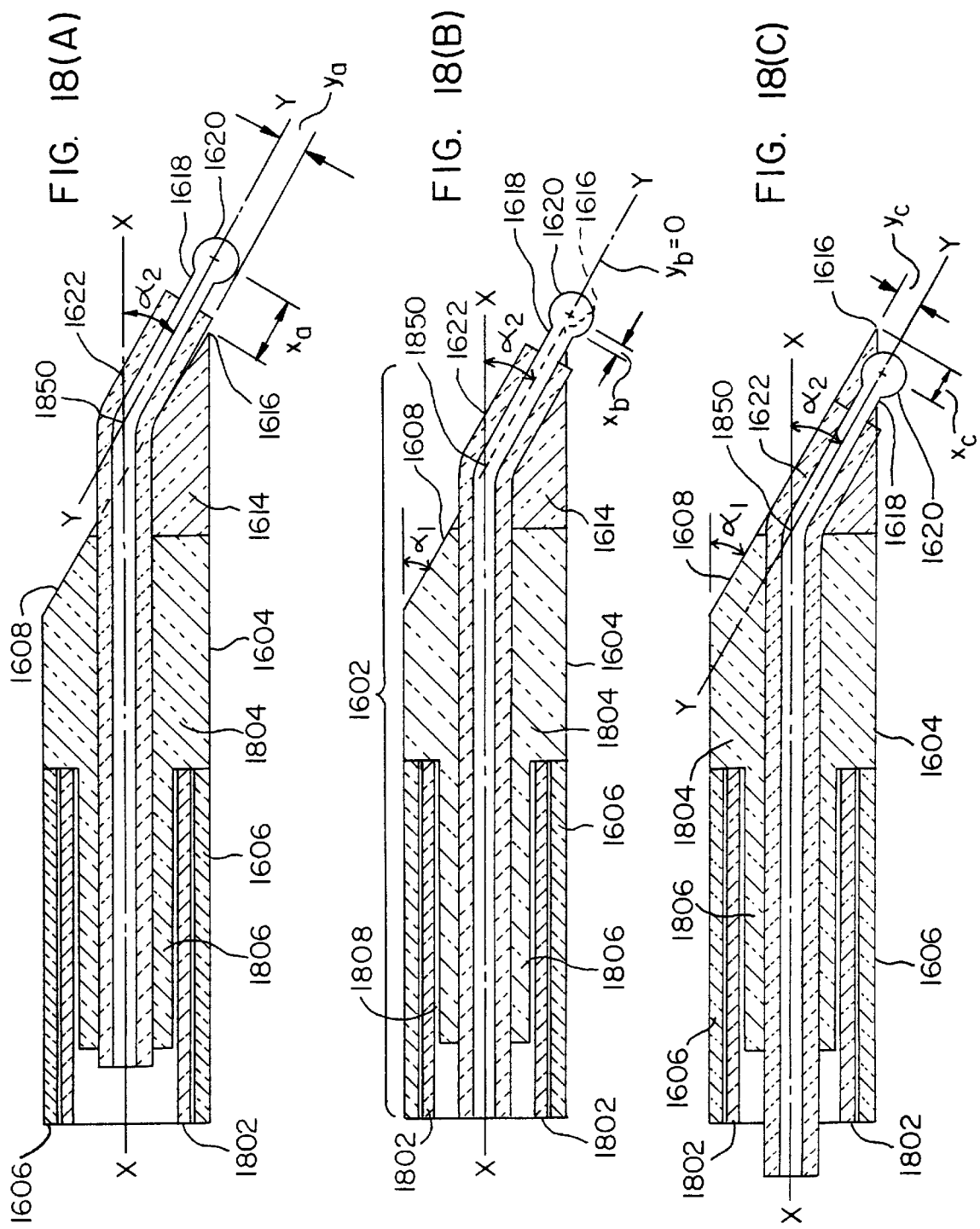

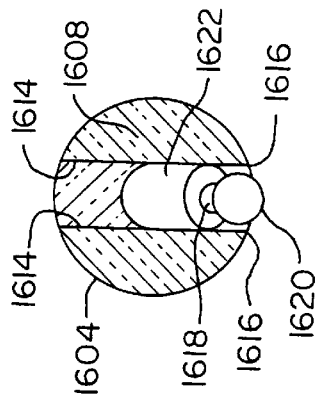
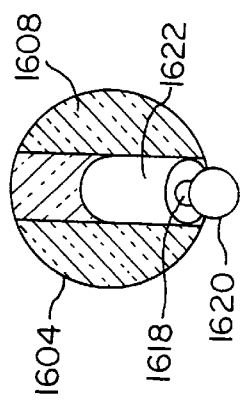
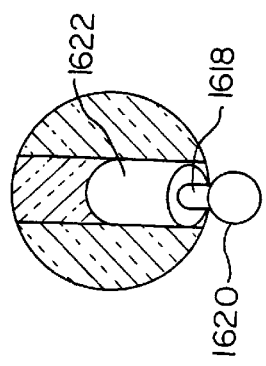
FIG. 20(A)  FIG. 20(B)  FIG. 20(C)
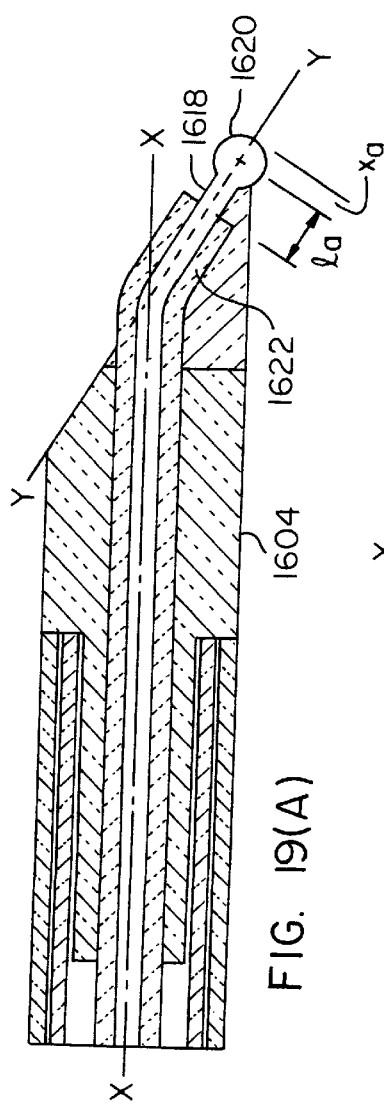
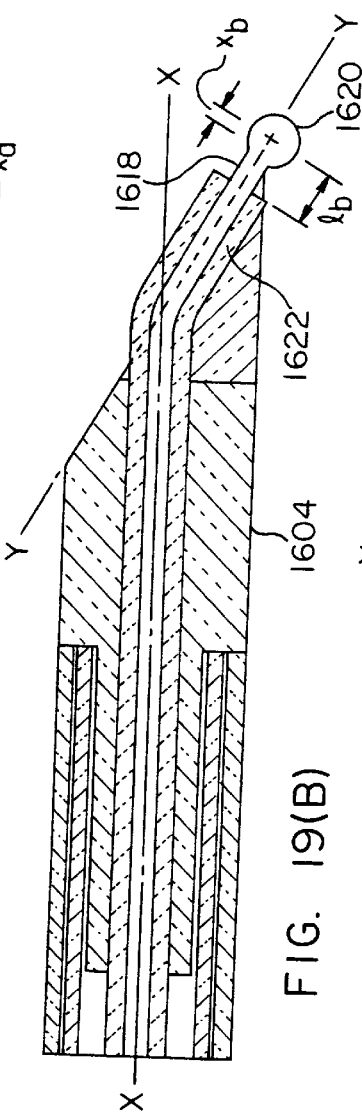
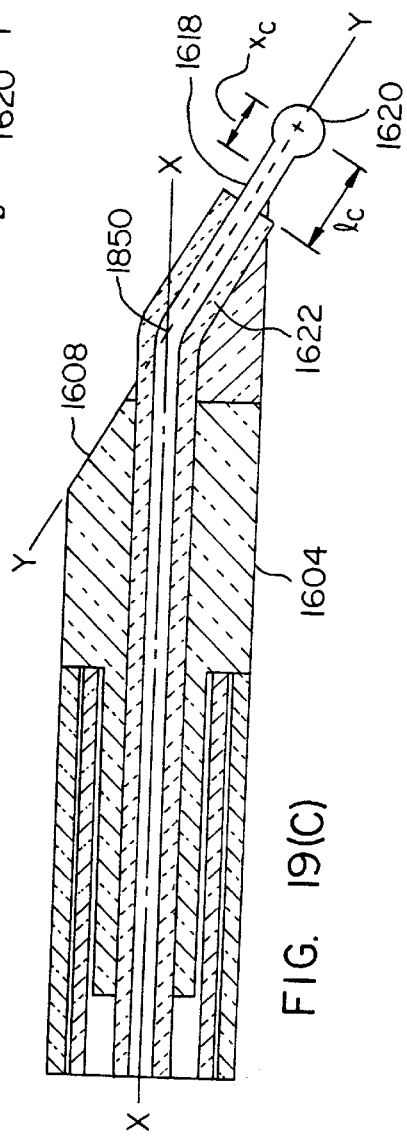
FIG. 19(A)  FIG. 19(B)  FIG. 19(C)

VERSATILE ELECTROSURGICAL INSTRUMENT CAPABLE OF MULTIPLE SURGICAL FUNCTIONS

This is a Continuation-in-Part of Ser. No. 329,342 Oct. 26, 1994 U.S. Pat. No. 5,556,397, which issued on Sep. 17, 1996.

FIELD OF THE INVENTION

This invention relates to an improved electrosurgical instrument capable of performing incisions and coagulating and cauterizing functions, and more particularly to a coaxial electrosurgical instrument which performs like and can be used as easily as a monopolar surgical instrument but which eliminates current flow through the patient like a bipolar surgical instrument and cuts through tissue at controlled rates which efficiently minimize related bleeding.

BACKGROUND OF THE RELEVANT ART

In recent times, the use of electrosurgical instruments to perform precise surgery has become widespread, mainly because it offers significant advantages over traditional scalpel surgery. For many surgical procedures, e.g., open heart surgery and laparscopic procedures, electrosurgery results in significantly less patient trauma. In neurosurgical procedures, because of the very sensitive tissue around the surgical site and the need to immediately limit bleeding, the facility to perform incisions and coagulations with a single electrosurgical instrument is highly advantageous. Similarly, in transurethral surgery, where the goal is to safely remove unwanted or diseased tissue from a PROSTATE gland, the operation is best done with an electrosurgical instrument because the surgeon has to operate through a relatively narrow bore resectoscope. In any such surgical procedure, while speed in precisely incising tissue is important it is equally important to promptly and effectively cauterize incised blood-carrying vessels to avoid obscuration of the surgical site.

It is well known that conventional electrosurgical instruments operate when an electrical path is completed between two electrodes. This requires that both electrodes be in some kind of electrically-conducting physical contact with the patient's body. The electrical current provided to such instruments is sinusoidal, i.e., neither electrode is either positive or negative relative to the other except instantaneously.

Most surgeons prefer to use electrosurgical instruments over traditional scalpels because the former are essentially "bloodless" knives. Such an instrument can dissect tissue while at the same time reducing the amount of blood loss by permitting quick coagulation of the dissected tissue. Cutting occurs when the current density is high enough to explode the tissue cells near the electrode, and the same instrument may have a portion usable to either seal an incised vessel or to accelerate the coagulation process.

As best seen with reference to FIG. 1, when the sinusoidal waveform of the applied current is continuous and at its maximum amplitude, a cutting effect is obtained due to intense, almost explosive heating of cells contacted by the active electrode due to the locally very high current density. To provide coagulation, a damped current waveform, comprising short bursts of current rather than a continuous current, may be provided to the tissue. This causes local cellular dehydration because of the smaller amount of electrical current and power delivered to the tissue. It allows the surgeon to obtain hemostasis, allowing him to destroy tissue masses, or to cause selective desiccation of tissue. For a blended operation the surgeon may apply a current having a waveform as indicated at the right portion of FIG. 1.

As schematically indicated in FIG. 2, providing continuous high amplitude current via a thin electrode can generate a pure cut, and applying a damped waveform can generate a blended cut in which there is incision of tissue as well as coagulation of any blood leakage nearby. By selecting an appropriately shaped active electrode tip, applying a low power flow and holding the tip in physical contact with tissue, the surgeon can cause local heating and desiccation of the tissue without necessarily causing tissue necrosis. Finally, by holding the electrode close to, but not in direct contact with the tissue while applying a high power flow, a surgeon can cause arcing between the electrode and the tissue surface to cause local charring to produce fulguration. This last technique is commonly used in cardiovascular and thoracic surgical procedures.

A monopolar instrument is one in which the electrical current flows from the active electrode, which may be shaped as a blade, a hook, or a straight ended wire, to an electrical "ground". A grounding pad is typically applied to the thigh, back or some other spot on the patient's body where contact may be made with a relatively large surface area. Thus, in monopolar electrosurgical instruments, the surface area of one of the two electrodes is deliberately made significantly larger than that of the other. This is done so that the current density is much greater at the electrode having the smallest surface area when in contact with the patient's tissue. In such applications, the electrode with the smaller surface area is referred to as the "active" electrode. There are, however, serious problems that arise when there are strong current paths established due to deterioration of electrical insulation, capacitive coupling in spite of intact insulation, and accidental arcing between the instrument body and the patient's tissue in regions not visible to the surgeon. Some of these can be solved by the use of electrical shielding between the monopolar surgical instrument and a metal cannula. Monopolar electrosurgery, however, requires that an electric current flow through the patient's tissues away from the surgical site.

The frequency of the electrical voltage used for electrosurgery of any kind is typically much higher than the conventional mains frequency of 60 Hz, often in the range 400,000 Hz to 3,000,000 Hz, a range commonly referred to as "radiofrequency". Radiofrequency is generally considered too high to stimulate muscular tissue and, therefore, is believed to be safe to the patient. However, because the electrical current must flow through a significant portion of the patient's body, the surgeon and staff are at some risk of being shocked because of capacitive coupling with the patient. Also, the high voltage/high frequency generator and the wire leading therefrom to the active electrode, can act as an electrical noise generator and may adversely affect sensitive instrumentation.

In light of the above-described problems with a monopolar instrument, a bipolar instrument is sometimes used. It requires no grounding pad to be applied to the patient, but instead employs two electrodes which mechanically oppose each other like the two halves of a surgical forceps. The instrument is used to squeeze tissue between the two electrodes as a current passes between them to cause coagulation. Thus, a bipolar surgical instrument normally is used only when coagulation is desired and when current flowing through the patient is clearly undesirable. The bipolar instrument is not used to dissect tissue in most cases because it does not permit the surgeon to do so with precision.

Reference to FIG. 3 shows various types of monopolar active electrode tip shapes as well as the general tip end structure of a bipolar instrument. FIG. 4 illustrates the general overall configuration of a bipolar instrument.

FIGS. 5(A)–5(C) schematically indicate the typical distributions of electrical lines of force and equipotential lines normal thereto (as broken lines): for a monopolar instrument having a single electrode contacting the tissue to be operated on; for a bipolar instrument with two electrodes between which current flows through the patient's tissue, and for a coaxial surgical instrument (CSI) as in this invention in which there is a single electrode coaxially surrounded by an outer electrode with the entire operative electrical field highly localized and contained therebetween.

The present invention, as described and claimed herein, relates to a particularly advantageous form of a generally coaxial surgical instrument and has the external form as generally illustrated in FIGS. 16(A) and 16(B) as explained more fully hereinbelow. Also disclosed are other variations.

SUMMARY OF THE INVENTION

It is a principal object of this invention to provide a versatile electrosurgical instrument of simple form which alone enables a surgeon to selectively perform multiple functions such as precise incisions, cauterization, and coagulation of a patient's tissue.

It is another object of this invention to provide a versatile electrosurgical instrument which facilitates performance of precise incisions, coagulation of tissue and/or body fluids and sealing of blood vessels, by a user selectively engaging the same with an active electrode.

It is yet another object of this invention to provide an electrosurgical instrument suitable for laparscopic surgery in confined or difficult locations within a patient's body without subjecting the patient's tissue to electrical currents except immediately at the surgical site.

It is a related object according to another aspect of this invention to provide a method of electrosurgically incising and/or selectively coagulating tissue during a surgical procedure with a single instrument.

It is another related object of this invention to provide a method by which a surgeon may perform multiple surgical functions, including incisions and/or coagulations with a coaxial electrosurgical instrument which facilitates clear and direct viewing of the surgical site, without passing electrical current through the patient's tissue except immediately at the surgical site.

These and other related objects of this invention are realized by providing an electrosurgical instrument which comprises an elongate, tubular, outer electrode covered with an insulating sleeve which leaves a distal end portion of the outer electrode uninsulated. An elongate inner electrode is located coaxially within the outer electrode and is electrically insulated therefrom. A distal uninsulated end portion of the inner electrode extends to a predetermined length from the distal uninsulated end portion of the outer electrode. This enables a user to make simultaneous electrical contact by the distal uninsulated end portions of both the inner and outer electrodes with the tissue to be operated on. Means are included for enabling the user to provide an alternating electrical voltage difference, at a controlled frequency, between the inner and outer electrodes. The distal end portion of the outer electrode preferably has a transverse end surface inclined at a first angle relative to a common axis of the inner and outer electrodes, the transverse end surface and an outer peripheral surface of the outer electrode intersect at an acute angle to form a leading edge of the outer electrode, a leading edge portion of the outer electrode has an axially oriented cutout extending inwardly from the leading edge, and at least a distal end portion of the insulating sleeve is located within the cutout.

In one aspect of the above-described invention, the distal uninsulated end portion of the inner electrode has a distal end bent sideways and has a smoothly rounded bulbous tip.

In another aspect of the invention, there is provided a method is of performing surgical operations, including incisions, cauterizations and coagulations of a tissue. This method includes the steps of providing an elongate tubular outer electrode covered with an outer insulating sleeve which leaves a distal end portion of the outer electrode uninsulated, and providing an elongate inner electrode located coaxially within the outer electrode and an inner insulating sleeve surrounding the inner electrode to electrically insulate the inner electrode from the outer electrode. A distal end of the inner insulating sleeve is located such that a distal uninsulated end portion of the inner electrode extends to a first predetermined length from the distal end of the inner insulating sleeve and has a rounded bulbous end to enable simultaneous electrical contact by the distal uninsulated end portions of both the inner and outer electrodes with the tissue to be operated on. The distal end portion of the outer electrode has a transverse end surface inclined at a first angle relative to a common axis of the inner and outer electrodes, the transverse end surface and an outer peripheral surface of the outer electrode intersect at an acute angle to form a leading edge portion of the outer electrode, and a leading edge portion of the outer electrode has an axially oriented cutout extending inwardly of the leading edge, and at least a distal end portion of the insulating sleeve is located within the cutout. The rounded bulbous end of the inner electrode and the distal uninsulated end portion of the outer electrode are simultaneously contacted to the tissue to be operated on and an alternating electrical voltage difference is provided at a controlled frequency between the inner and outer electrodes. This causes a high frequency, high density, current to flow substantially only through that portion of the contacted tissue which lies between tissue-contacting surfaces of the inner and outer electrodes.

BRIEF DESCRIPTION OF THE DRAWING

FIG. 7(A) is a longitudinal cross-sectional view of the distal operating end of a coaxial electrosurgical instrument according to co-pending U.S. application Ser. No. 08/505,543, and is one in which the coaxial inner electrode has a bent end part; FIG. 7(B) is an external side view of the same portion of the instrument; and, FIG. 7(C) is an end view looking toward the electrodes in the same embodiment.

FIGS. 8(A), 8(B), and 8(C), are respective longitudinal cross-sectional, side and end views of another preferred embodiment of the invention per U.S. Ser. No. 08/505,543, supra, in which the inner electrode has an entirely straight end extending outwardly of the coaxial outer electrode.

FIG. 12 is a first side view of a variant, according co copending U.S. application Ser. No. 08/505,543 in which the coaxial inner electrode has an angled distal end part with a smoothly rounded bulbous tip.

FIG. 13 is a second side view of the invention per FIG. 12, but at a 90° displacement relative thereto, also about a longitudinal axis thereof.

FIG. 14 is a longitudinal view corresponding to FIG. 13.

FIGS. 18(A), 18(B) and 18(C), respectively, are three longitudinal cross-sectional views of the electrosurgical instrument according to the preferred embodiment, each showing a different dispositional relationship, in an axial direction, between an inner and an outer electrode.

FIGS. 19(A), 19(B) and 19(C), respectively, are three more longitudinal cross-sectional views of the preferred invention, to show different variations in dimensions and disposition of the uninsulated portion of the inner electrode in relation to the outer electrode.

FIGS. 20(A), 20(B) and 20(C), respectively, are end views corresponding to FIGS. 19(A), 19(B) and 19(C).

DETAILED DESCRIPTION OF THE PREFERRED EMBODIMENTS

Figure 1:
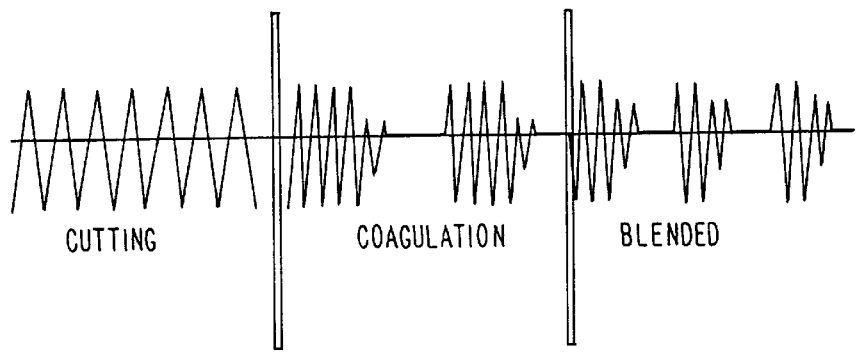
FIG. 1 is a graphical plot showing electrical current waveforms suitable for use during cutting, coagulation, and blended surgical operation with an electrosurgical instrument of any kind.
Figure 2:
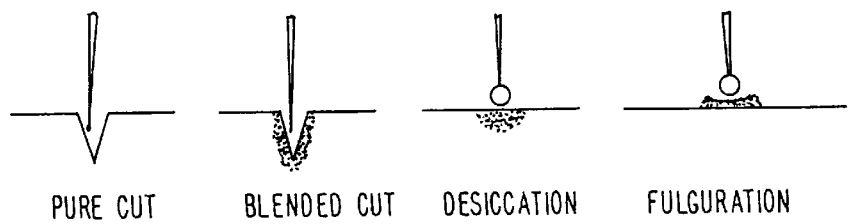
FIG. 2 shows in schematic form how differently shaped monopolar electrosurgical instrument tips may be used to perform a pure cut, a blended cut, desiccation of a tissue, or fulguration.
Figure 3:
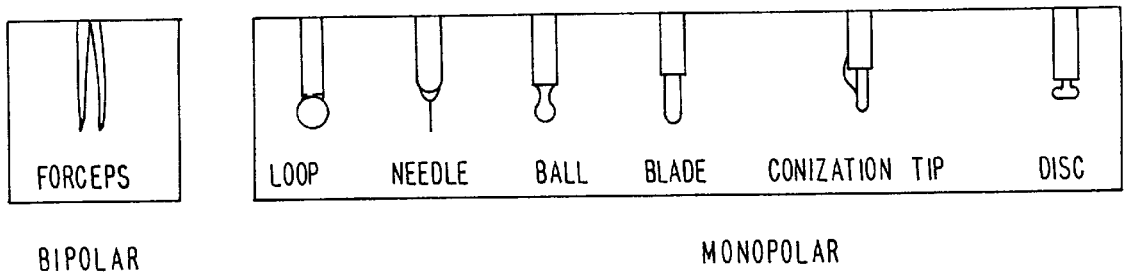
FIG. 3 shows exemplary active electrode tip shapes for monopolar and bipolar electrosurgical instruments of known type.
Figure 4:
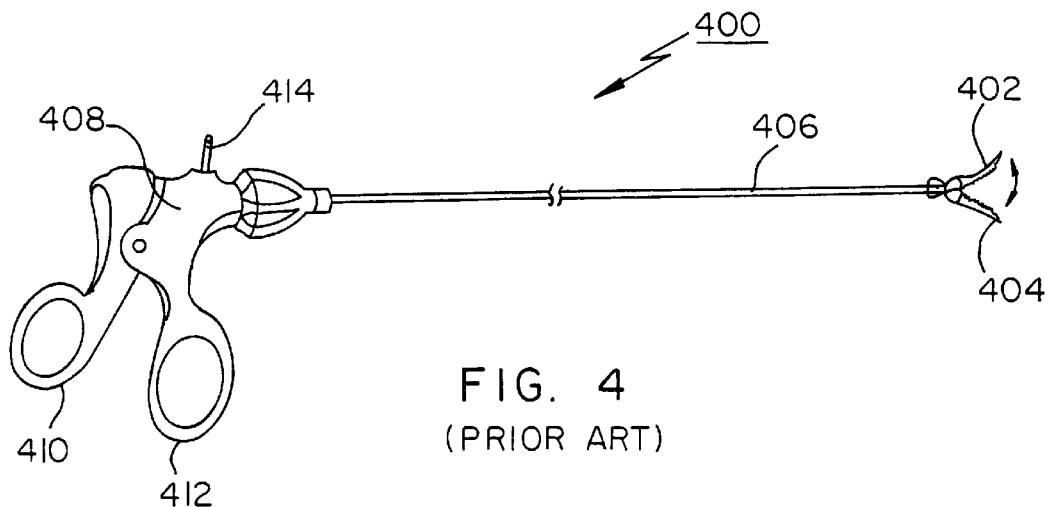
FIG. 4 is a side view of a bipolar electrosurgical instrument of known type.

FIG. 4 illustrates in side view a known bipolar electrosurgical instrument 400 which comprises two coacting and pivotably related elements 402 and 404, mounted at a distal end of an elongate tubular body element 406. A proximal end of this elongate body 406 is coupled to a hand-held, user-graspable, scissors-like handle 408 which comprises two pivotably cooperating elements 410 and 412 connected by suitable linkages to obtain corresponding pivoting movement between electrode elements 402 and 404 in known manner. Note cable 414 which, in use, would be connected to a source of controlled electrical power input and has individual wires connected to electrode elements 402 and 404.

Figures 5A, 5B, 5C:
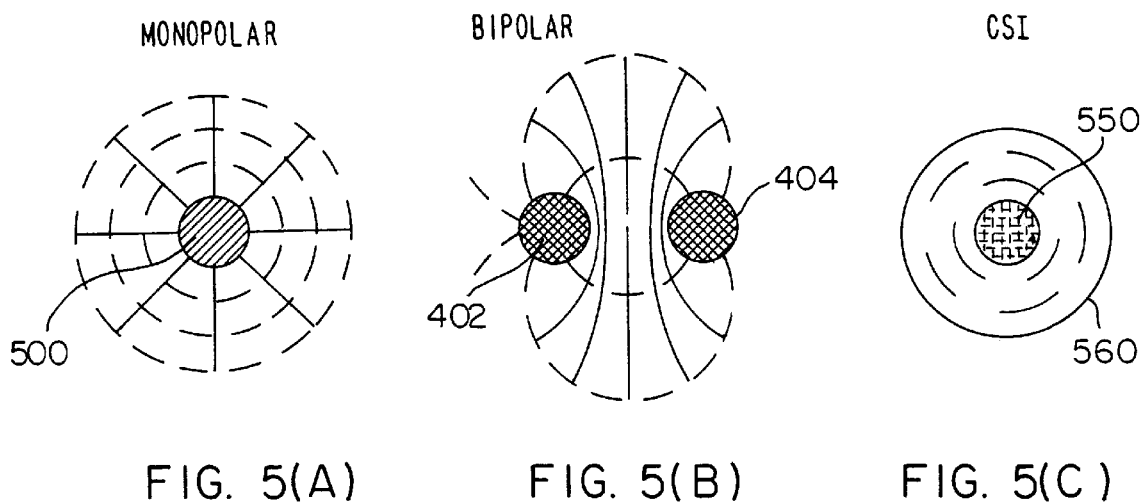
FIGS. 5(A)–5(C) present schematic views of the distributions of electric lines of force and equipotential lines for monopolar, bipolar, and coaxial surgical instruments (CSI), respectively.

FIG. 5(A) schematically illustrates by solid lines an electrical field about the single electrode 500 of a monopolar electrosurgical instrument. The electric field and time-varying electric currents extend through the tissue of the patient away from the single electrode 500. The electric lines of force are shown as solid lines and the equipotential lines as broken lines.

For a bipolar electrosurgical instrument comprising two cooperating electrodes, for example 402 and 404, when both electrodes are in contact with the patient's tissue, the (solid) electric lines of force between these two electrodes and the equipotential lines (broken) are as best seen in FIG. 5(B). Of necessity, electric current will tend to be experienced by the patient's tissue at locations away from the cooperating electrodes 402 and 404.

Finally, with a coaxial electrosurgical instrument comprising an inner electrode 550 and a coaxially surrounding outer electrode 560, the electric field is confined to be within the region between these two electrodes, as indicated in FIG. 5(C).

An advantage of the coaxial electrosurgical instrument is that it has a very limited region within which an electric current has to flow through a patient's tissue in order to perform its intended functions of incision, coagulation, or cauterization. Therefore, by making the respective diameters of the inner and outer electrodes small enough, a surgeon using the instrument can very severely limit the amount of tissue affected by electric current generated by contact with the electrodes at the operating distal end of the instrument. For neurosurgery, cardiovascular procedures, and the like, this is either highly desirable or, in some cases, vital.

Figure 6:
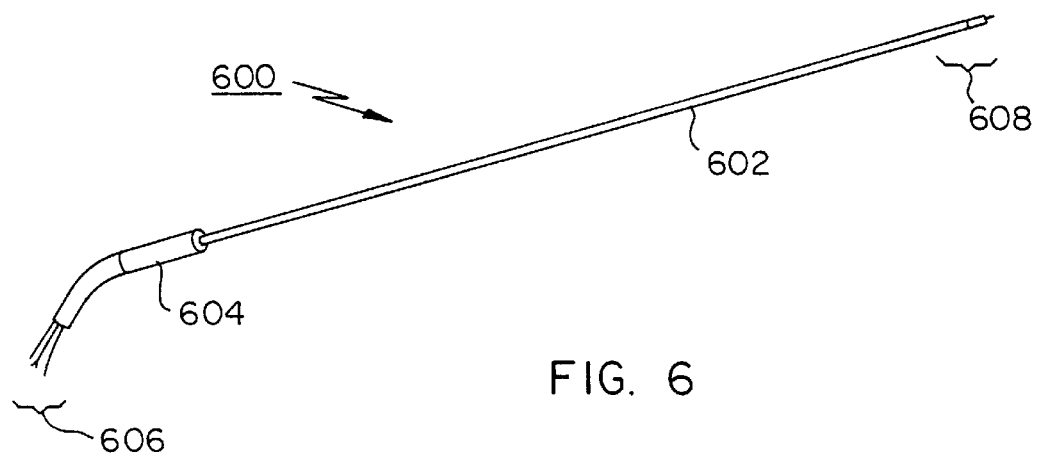
FIG. 6 is a side view of a coaxial electrosurgical instrument according to a preferred embodiment of this invention.

As best seen in FIG. 6, the coaxial electrosurgical instrument 600 according to this invention has a long, thin tubular body 602 (much like the elongate body 406 of the bipolar instrument 400 illustrated in FIG. 4) but a much simpler hand-held, user-graspable handle 604 through which electrical wiring 606 provides electrical power to the distal operating end 608 of the instrument. In use, therefore, a surgeon would hold the handle 604 and, by any conventional means, e.g., a thumb, foot, or otherwise operated switch, control the intensity, waveform, and duration of an electrical power supplied to the operating electrodes. This is discussed in greater detail in the following paragraphs.

FIGS. 7(A), 7(B) and 7(C) are related to a first preferred embodiment according to U.S. Pat. No. 5,556,397, and provide a detailed understanding of the operating end portion 608 of an instrument like that illustrated generally in FIG. 6. It should be appreciated that the actual instrument may be several inches long, and that means of any suitable known type for controllably providing electrical power may be employed. In other words, it is the structure and functionality of the distal operating end of the instrument which is of significance and provides distinct advantages over the prior art. The manner of connecting the electrical power supply and controlling the electrical power flow therefore may be of known type and, while important, are not considered determinative of the novelty of this invention.

As best seen in FIG. 7(A), the distal end portion 608 of the instrument has a substantially coaxial structure around longitudinal axis X—X. This structure includes a cylindrical, wire-like, electrically conductive inner electrode 702 coaxial about axis X—X. For most of its length along the instrument 600, inner electrode 702 is provided with an electrically insulating sleeve 704 to ensure against electrical shorting with respect to other elements.

Around the same axis, and coaxially surrounding inner electrode 702, is a conductive outer electrode 706 having the form of a thin elongate tube. At the distal end of outer electrode 706 there is fitted an electrically conducting tip element 708 which may be press-fitted or otherwise made virtually integral with the tubular structure of outer electrode 706. An insulating sleeve 710 is provided over the outer cylindrical surface of outer electrode 706 at least to the very end where the tubular outer electrode body 706 ends fitted tightly to tip element 708.

Tip element 708 is generally cylindrical and has a reduced diameter portion 712 sized and shaped to be fitted to the end of tubular outer electrode 706 in intimate electrical contact therewith. Tip element 708 also has an uninsulated exposed end portion 714 which preferably has the same outer diameter as tubular body 706, although this is not essential.

Tip element 708 is preferably cut at its end so as to have an inclined end face 716 which makes an acute angle "α" with respect to central axis X—X. As a consequence, end face 716 has a generally annular elliptic shape, as best seen in the view of FIG. 7(B).

The inside diameter of tip element 708 is made larger than the outside diameter of insulating sleeve 704 provided around inner electrode 702. An insulating cylindrical insert 718 is press fitted into tip element 708 and is shaped at its inner end so as to receive an extreme distal end portion of insulating sleeve 704 surrounding most of the length of inner electrode 702. Insert 718 is formed at its outermost end so that it has an angled face coplanar with the angled end face 716 of tip element 708. Therefore, closely surrounding the extreme distal end portion of inner electrode 702 there is the inclined end face 720 of insulating central insert 718 which virtually acts as a sliding journal bearing for the distal end portion of inner electrode 702.

Projecting outwardly of the plane of end faces 720 and 716 is a predetermined length 722 of inner electrode 702 which in this instrument is straight and coaxial with axis X—X.

As best seen in FIGS. 7(A), 7(B) and 7(C), this projecting portion of the inner electrode 702 is bent so that an extreme end part 724 thereof is virtually at 90° with respect to access X—X. The exact shape of the bend or curve involved is considered a matter of design choice, the key being that there is a sufficient length of portion 724 to enable a user to hook a portion of the tissue which is to be operated on by the device.

In the instrument per FIGS. 7(A), 7(B) and 7(C), this end part 724 of inner electrode 702 ends in an end face 726 which does not extend radially, relative to axis X—X, any further than the outside surface of tip element 708. Tip element 408 has the same external diameter as the outer surface of the outer electrode 706. Persons of ordinary skill in the art may be expected to cause the end part 724 to be somewhat shorter or somewhat longer depending on particular applications of interest. There are certain advantages to the embodiment as illustrated in FIGS. 7(A), 7(B) and 7(C), as discussed more fully hereinbelow.

Another structurally somewhat simpler embodiment is illustrated in FIGS. 8(A), 8(B) and 8(C). The only significant difference between this second embodiment and the embodiment per FIGS. 7(A), 7(B) and 7(C) lies in the fact that in the second embodiment the inner electrode is entirely straight all the way through to its end face 826 which is preferably at right angles to the common access X—X. All the other elements, particularly the insulating sleeves 704 and 710 (of the inner and outer electrodes 702 and 706, respectively), the tip element 708, and the like are exactly the same in shape and function as in the preferred embodiment according to FIGS. 7(A), 7(B) and 7(C). Thus, insulating insert 718 in both embodiments has an angled end face 720 coplanar with the angled end face 716 of tip element 714, and serves as an insulating sliding journal bearing for inner electrode 702.

The only distinction between the two embodiments, in terms of structure, is that the embodiment per FIGS. 8(A), 8(B) and 8(C) does not have a bent end part.

A detailed discussion will now be provided of the advantageous manner in which the instrument per FIGS. 7(A), 7(B) and 7(C) may be employed in surgery in a very confined space, as in a laparscopic procedure where finely controlled incisions to a predetermined small depth must be made. An example is where there is trauma or disease which requires very careful isolation of portions of organs physically close to a small bowel in a person's abdomen. Careless incision can cause bleeding and peritonitis, and improper use of monopolar or bipolar surgical instruments can result in damage to fragile tissues. It is in circumstances like these that the preferred embodiment provides unique advantages.

Figure 9:
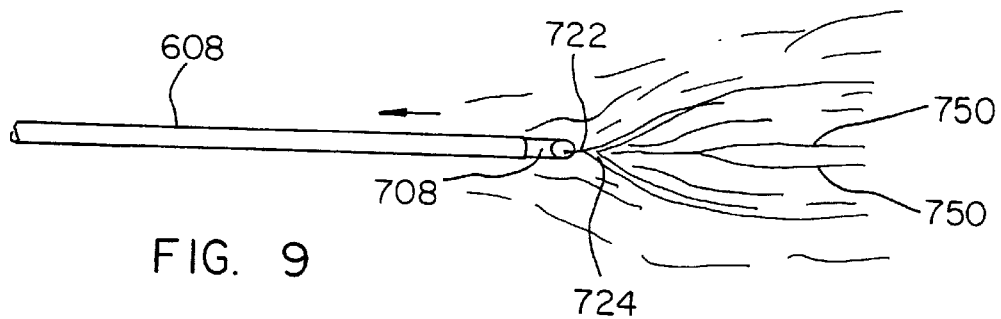
FIG. 9 is a view schematically illustrating how the bent end of the inner electrode according to the preferred embodiment per FIGS. 6, 7(A), 7(B) and 7(C) may be used to make an incision into tissue, with the operating inner electrode distal end part and the tissue being cut thereby clearly visible.

As best seen in FIG. 9, the surgeon applies a downward pressure on tissue with the outer surface of tip element 708 and a pulling force simultaneously to the body 608 of the coaxial electrosurgical instrument per the preferred embodiment, with the angled face 716 uppermost where it can be viewed easily. The extended portion 722 of the inner electrode is then pointing away from the surgeon and bent part 724 thereof is pressing into the tissue which is to be incised.

Figure 10:
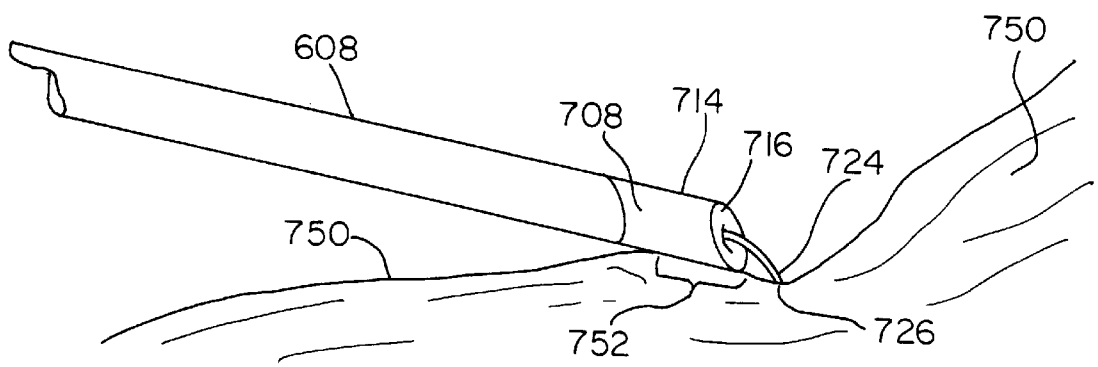
FIG. 10 is an enlarged perspective view of the operating end of the instrument per FIGS. 7(A) and 7(B) in use, either at the initiation of a cutting operation or as it would be used to provide local coagulation or catheterization.

As best seen with reference to FIG. 10, the end part 424 of inner electrode 702 is then making electrical contact at its end surface 726 with tissue 750. In the just-described disposition of the elongate body 608 of the instrument, a lower portion of the outer surface of tip element 708 is pressed to the tissue at the side where inclined face 716 makes an acute angle with the outer cylindrical surface thereof, and a small zone 752 of the tissue is depressed. There is good electrical contact between the conductive tip element 708, i.e., the outer electrode in effect, and simultaneously by the bent part 724 of inner electrode 702.

When the surgeon now applies a controlled potential difference between the electrodes, a current will flow through only that portion of the tissue which is located between the inner and outer electrodes. Since this tissue is already under physical pressure due to contact at 752, a clean narrow incision may be made by providing a suitable electrical power flow. This is indicated generally in FIG. 9. The result is that the tissue 750 is incised by the very high current density immediately between the bent part 724 of the inner electrode and the adjacent angled surface 716 which is part of the outer electrode.

It is important to appreciate the fact that because the applied potential difference is of a time-varying oscillating nature, neither the inner electrode 702 nor the outer electrode 706 is permanently positive or negative relative to the other. The high frequency time-varying electrical potential difference between the electrodes, when both are in conductive contact with the tissue, will result in a corresponding time-dependent electrical current flowing between the end part 724 and the inclined surface 716, respectively, of the inner and outer electrodes 702 and 706.

In the structure illustrated in the above-described figures, it is clear that the uninsulated exposed outer surface area of the outer electrode, essentially the cylindrical surface 714 and the end face 716 of the tip element 708, is considerably larger than the uninsulated area of the exposed straight portion 722 and the bent part 724 (including end face 726) of the inner electrode 702. Because of this disparity in surface area sizes, the current density immediately surrounding the bent part 724 and the end face 726 of the inner electrode 702 will be very high and will cause explosive disruption of the contacted tissue cells, resulting in clean hemostatic cut, provided electrical power is delivered in an amount and at a frequency suited to the particular tissue. In other words, to make the same cut through a denser tissue may require a higher power input or frequency as compared to, say, a softer and more moisture-laden tissue. The exact values of the current electrical power and the frequency at which it is delivered must be matters of choice for the surgeon in light of exigent circumstances.

As will be readily appreciated, the surgeon could turn the tool 180° relative to the above-described mode of application, so that a patient's tissue is contacted by the outer surface 714 of tip element 708, i.e., by the outer electrode 706, as well as by the curved outer surface the bend in the uninsulated portion of the inner electrode 702. There would be no hooking of the tissue under these circumstances, but upon delivery of the right amount of electrical power at the right frequency a surgeon may be able to make incisions. The difference is that in the first-described disposition it was the narrow leading wedge-shaped portion of the tip element 708 which depressed the tissue at 752 and allowed the surgeon a clear view of how and where the bent part 724 of the inner electrode was performing its cutting function.

As noted earlier, it is well known that by appropriate control on the electrical power delivered, and/or the frequency at which the current is generated, the same electrode may be used to coagulate tissues and/or any bodily fluids present contacted. Similarly, by appropriate variation of the electrical power and/or the frequency at which it is provided, cauterization of vessels carrying bodily fluids may be obtained.

Figure 11:
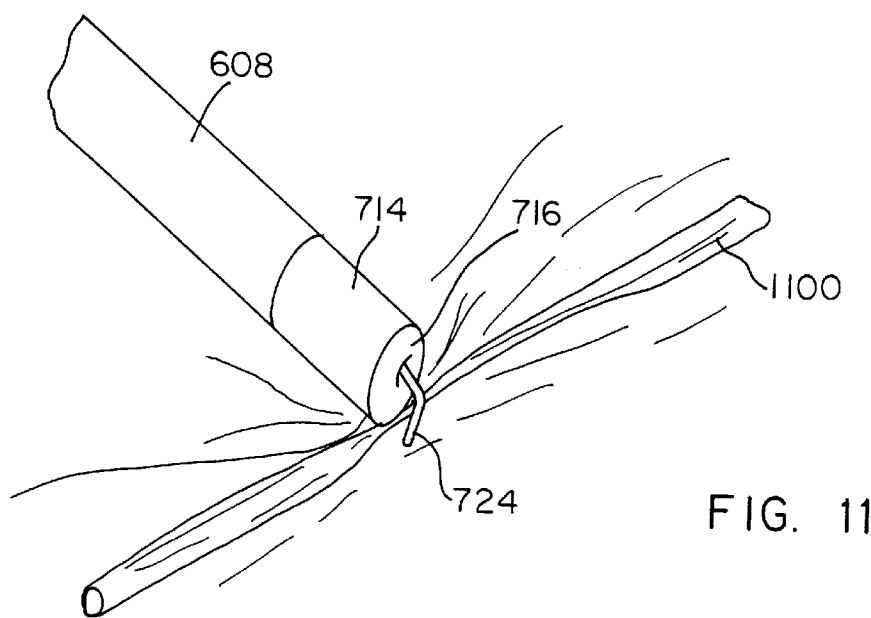
FIG. 11 is a further enlarged view of the instrument per FIG. 10 to illustrate a manner of its use to hook a blood vessel in a patient to apply energy to cauterize the same.

FIG. 11 illustrates one such procedure with the embodiment per FIGS. 7(A), 7(B) and 7(C). In this application, the surgeon employs the bent part 724 to hook over a blood vessel 1100. By tugging on the blood vessel in this manner, the surgeon can cause local collapse of the walls of the vessel and, by appropriate delivery of electrical power generate a local electrical burn and sealing of the vessel. By doing this at two points, and thereafter incising therebetween at a higher power rate or frequency, the surgeon can cut through the vessel without permitting leakage of its contents at the surgical site. These and other variations will become readily apparent to surgeons utilizing the tool as they gain greater familiarity with its effectiveness.

The embodiment per FIGS. 8(A), 8(B) and 8(C) can be used to perform substantially the same sort of functions of incision, coagulation, and cauterization as described with respect to the preferred embodiment per FIGS. 7(A), 7(B) and 7(C). The only distinction is that there is no bent part with which to hook tissue, so that there has to be pressure applied by the outer cylindrical surface of that portion of the inner electrode 702 which extends beyond the inclined end face 716 of the outer electrode, i.e., the tip element 708 thereof. Thus, with this embodiment it would not be possible for a surgeon to hook a blood vessel as was possible with the embodiment described with reference to FIG. 11. Nevertheless, for certain types of operations a surgeon may wish to perform incisions of very limited depth without running the risk of accidentally hooking a fine blood vessel or tissue weakened by disease or trauma. For such applications, and with obvious variations of circumstances, it may be preferable to use the embodiment per FIGS. 8(A), 8(B) and 8(C).

When either of these embodiment is used in laparscopic surgery, conventional fiber optic viewing instruments, TV monitors, view enlargement devices or the like may be used exactly as with monopolar or bipolar instruments of known kind.

Both inner electrode 702 and outer electrode 706, as well as tip element 708, may be made a non-corrodible metal such as stainless steel. Insulating sleeves 704 and 710, as well as insulating insert 718, may be made of a known chemically inert electrically insulating material such as Teflon™ or nylon.

Experimental studies have shown that the embodiment per FIGS. 7(A)–7(C) is very efficient at cutting through body tissues, particularly soft tissues which are rich in electrolyte-containing fluids through which the applied current readily passes in a very small zone between the uninsulated end portions of the inner and outer electrodes 708 and 722. In fact, the cutting action sometimes is so efficient that the surgeon may have to deliberately slow down in order to cauterize severed circulatory vessels and/or to coagulate incidentally released body fluids such as blood in additional operational steps. Where the surgeon is working in a very confined zone of the body, and particularly when he or she must work rapidly and with a clear view of very sensitive tissue, e.g., in neurosurgery, this may pose a serious problem. A modified form of the structure has therefore been developed to improve the cauterization and coagulation capability of the device without sacrificing any of the other advantages, e.g., speed, flexibility in performing incisions, coagulation and cauterization without changing instruments, ability to operate in very confined quarters, and the like. This embodiment is particularly suitable for surgery performed laparscopically as it makes it easier to keep both the inner and outer electrodes in contact with the tissue being operated on and to modulate the applied electrical power during use.

As best understood with reference to FIGS. 12 and 13, in the instrument per embodiment 1200 disclosed and claimed in co-pending U.S. application Ser. No. 08/505,543, the most noticeable structural difference as compared with the embodiment per FIGS. 7(A)–7(C), is in the physical form of the extreme distal end portion of the inner electrode 722. Since numerous other elements and features of the structure are exactly the same as in the instrument per FIGS. 7(A)–7(C), the same numbering system will be employed to identify such common counterpart elements and features in FIGS. 12–14.

In the instrument according to FIGS. 7(A)–7(C), the distal end portion of inner electrode 702 was contained within and surrounded by an insulating cylindrical insert 718 press-fitted into tip element 708 at the end of the outer electrode 706, and insert 718 was formed at its outermost end to have an angled base coplanar with the angled end face 716 of tip element 708. The same structure could be employed in the instrument per FIGS. 12–14, but these figures illustrate yet another acceptable option. In this option, instead of an insulating sleeve 704 and a separate coaxial insulating cylindrical insert 718 at the end, there may be provided a single cylindrical insulating element 1218 tightly fitted to the outer surface of the inner electrode 702. This insulating element 1218 extends just slightly beyond the angled surface 716 of tip 708.

That portion of inner electrode 702 which extends beyond and outwardly up the end of insulating element 1218 is preferably but not necessarily angled to be substantially parallel to slanted end face 716, i.e., at approximately the same angle "α" relative to their common axis X—X (see FIG. 7(C)). This angled distal end portion 1224 is sized so that a portion of it extends forwardly of the leading edge where slanted face 716 and the cylindrical outer surface of tip 708 intersect at the leading edge 1230. Furthermore, the very distal end of angled end portion 1224 of inner electrode 702 is formed to have a smoothly rounded bulbous end 1250 which has a smooth, substantially spherical, curved surface 1260 extending forwardly of leading edge 1230 and also extending outwardly of the outer cylindrical surface of tip 708 in a radial direction. Preferred but not limiting dimensional relationships of the distal end portion of such an embodiment are best understood with reference to FIG. 15.

As best seen in FIG. 13, inner electrode 702 has the form of a thin straight wire contained within insulating element 1218 to be electrically insulated from and coaxial with cylindrical tip element 708 of the outer electrode. The uninsulated exposed portion 722 of inner electrode 702 is preferably angled so that a distal end portion 1224 thereof lies substantially parallel to angled end face 716 of tip element 708.

In the instrument per FIGS. 12–15, by any conventional means such as locally heating the end of portion 1224 with a sufficiently hot flame or otherwise, the very distal end material is formed to have a smoothly rounded bulbous shape integral with the distal end portion 1224. This bulbous end 1250, due to the surface tension of the molten material when locally heated, will have a virtually spherical shape with a smooth curved outer surface 1260.

Figure 15:
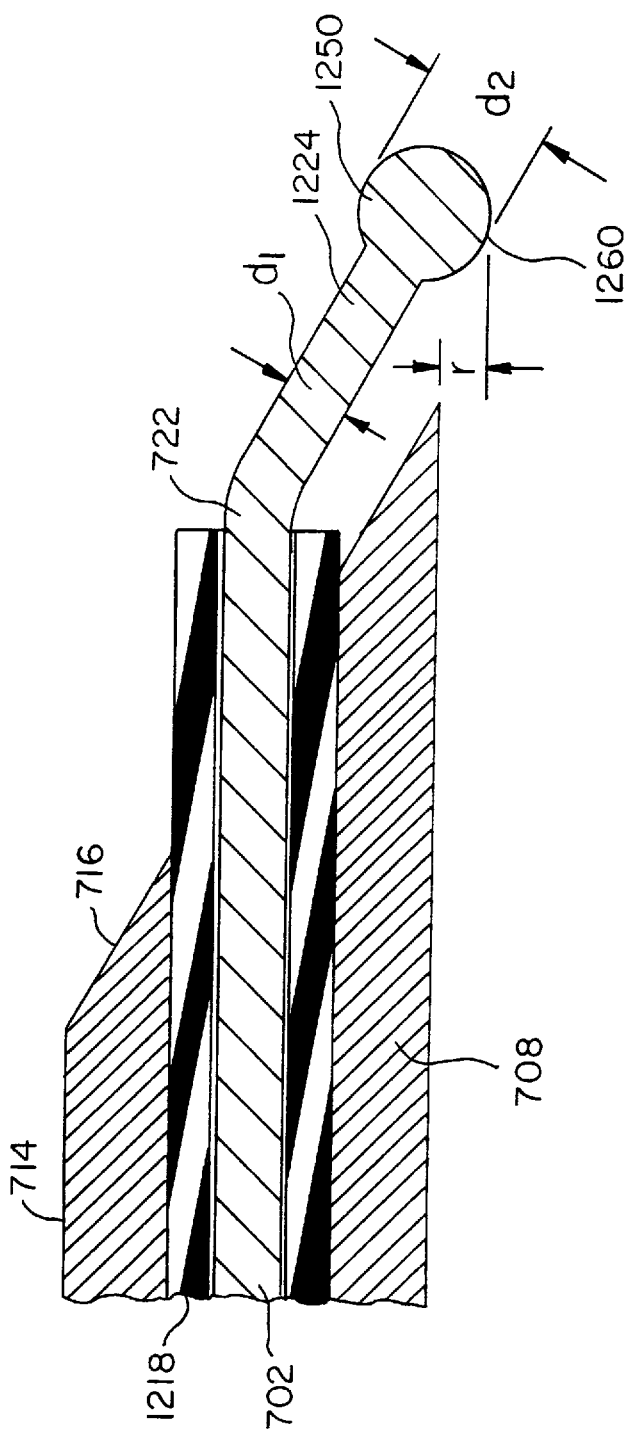
FIG. 15 explains the dimensional relationships and relative dispositions of the distal end portion of the third preferred embodiment per FIGS. 12–14.

As best seen in FIG. 15, with a diameter "$d_1$" for the inner electrode distal portion 1224, it is preferred that the bulbous end 1250 be formed to have a diameter "$d_2$" which is at least twice the size of "$d_1$". Furthermore, it is preferred that the smooth curved surface 1260 extend radially outward of the cylindrical outer surface of tip element 708 by a distance "r" which is preferably not less than one half of "$d_1$". These are the preferred dimensional relationships and, while not intended to be limiting, are considered desirable for reasons provided in the following paragraphs.

The basic mode of operating the instrument according to FIG. 15 is the same as that described earlier. Basically, what is required is that both the outer uninsulated exposed surface of tip 708 of the outer electrode and the exposed uninsulated portion of the inner electrode make simultaneous physical and electrically-conductive contact with the patient's tissue at the selected surgical site. Then, when a high frequency alternating current is passed between the two electrodes, the resulting current passes substantially only between the leading edge 1230 and the immediately adjacent surface portion of the bulbous end surface 1260 of the inner electrode.

By suitable control over the electrical power thus supplied between the two cooperating electrodes and the tissue therebetween, the operating surgeon can use the current passed through the tissue between the inner and outer electrodes to effect physical destruction of the tissue to create an incision. The goal, as discussed above in detail, is always to prevent passage of this electrical current through any more of the patient's body than the tissue which is to be incised. The effectiveness of the apparatus therefore depends on two principal factors: first, that both electrodes be in electrically conductive contact exactly as, when, and where desired by the surgeon; and, second, that the total surface area of tip 708 of the outer electrode in contact with the patient's tissue be significantly larger than the comparable tissue-contacting uninsulated exposed surface area of the inner electrode. If the disparity in the two respective tissue-contacting surface areas is sufficiently large, the desired incision will be performed very efficiently and, perhaps, too quickly to avoid leakage of body fluids to an undesired extent at the surgical site. It is not, however, desirable to make the inner electrode thicker to thereby provide it with a relatively large uninsulated tissue-contactable exposed surface area.

The solution provided as best understood with FIG. 15, is to cause the very end of the exposed portion of the inner electrode to have an enlarged surface area. This is done most economically and efficiently by temporarily causing local melting of the material of the inner electrode at its very end and then cooling it, the resulting shape being, as illustrated, a virtually spherical smooth curved bulbous end. By careful bending and placement of the inner electrode within the insulating element 1218 which is itself tightly fitted into the hollow interior of tape element 708, in a manner well understood by persons of ordinary skill in the art of microengineering, it is relatively easy to ensure that the smoothly curved surface 1260 is located so that a portion thereof extends radially outward of tip element 708 by a selected small distance "r".

As indicated in chain lines in FIG. 13, when the device is applied to tissue 1310, e.g., the lining of the stomach or intestine of a patient, a portion 1320 of the tissue pressed within the gap between leading edge 1230 of the outer electrode tip and the curved bulbous end surface 1260 of the inner electrode is in effect gently hooked or caught there. If the surgeon then applies an incising current, only this tissue will be primarily affected.

With the structure described in the immediately preceding paragraphs, the surgeon easily makes physical contact with tissue at a surgical site with both the outer electrically conductive surface of tip element 708 (a relatively large surface area) and the smoothly curved surface 1260 of bulbous end 1250 of the inner electrode (a smaller surface area) in the immediate vicinity and in front of the leading edge 1230. Just enough surface areas of the two electrodes contact the tissue to permit a controlled and even but not overly rapid incision to be made through the commonly contacted tissue by passage of the controlled electrical current (as described earlier) between the two electrodes in the small gap between leading edge 1230 and the immediately adjacent smoothly curved surface 1260 of the inner electrode.

By suitable control of the frequency variation and magnitude of the applied current, and with the provision of the smoothly curved somewhat enlarged surface at the end of the inner electrode, is found that the surgeon can very effectively coagulate adjacent body fluids and, as previously described, also obtain cauterization of any incidentally incised circulatory vessels, e.g., small arteries and veins.

In summary, with the instrument per FIGS. 12–15 the surgeon has the ability to smoothly incise, coagulate incidental fluids, and cauterize tissues at a very confined surgical site with a single instrument simply by adjusting the powered input to the device as and when needed. This is found to be less stressful to the surgeon and of particular help where highly sensitive tissue must be operated on, e.g., in neurosurgery, in laparscopic surgery when the surgeon has to be guided by optically obtained and displayed images rather than direct line-of-sight viewing, and where due to trauma or otherwise there is a tendency for the tissue to leak excessive amounts of body fluids.

Experimental tests and theoretical analysis lead to the conclusion that making the tissue-contactable uninsulated surface area of the inner electrode 702 at least less than half the corresponding tissue-contactable uninsulated area of the outer electrode 706 (i.e., the surface corresponding to its integral tip-element 708) will ensure good current density.

As will be appreciated by persons of ordinary skill in the surgical arts, with each new and advantageous electrosurgical tool that becomes available the burden shifts to the surgeon to learn how to use it optimally. In fact, surgeons may often develop highly creative solutions to known problems and may develop techniques for using the newly invented instruments which go beyond the inventor's expectations. Likewise, inventions to provide improved surgical tools require evaluation of feedback and an appreciation for the surgeon's practical needs. The present application must be understood in such a context, and the embodiments discussed in the following paragraphs with particular reference to FIGS. 16(A)–20(C) must be understood as intended to be the results of a continuing effort to ease the surgeon's task.

As noted earlier, the key to success of the various embodiments disclosed in this application is to ensure that there is simultaneous, effective, and continuing contact by the uninsulated portions of both the inner and outer electrodes with the tissue to effect a surgical procedure, e.g., incision of tissue, coagulation of bodily fluids, or cauterization. Thus, for example in conducting an incision within a confined space in the patient's body, with limited lighting and viewing capabilities, it is sometimes difficult for the surgeon to be certain he or she has "hooked" the tissue to be treated (in the sense in which earlier described herein). The desired simultaneous contact with that tissue by the uninsulated distal end portions of both the inner and outer electrodes must then be maintained to flow a controlled high frequency current substantially only through the simultaneously contacted tissue which lies between the contacting uninsulated surfaces of the electrodes. Until the surgeon has become fully comfortable with the form, the response time, and the method of functioning of the electrosurgical instrument, and sometimes even then and even for a highly proficient surgeon, maintenance of the required simultaneous contact may be difficult.

One way to ensure such contact with the embodiments per FIGS. 7(A)–14, at least for certain surgical operations, is for the surgeon to literally "hook" the tissue of interest with the distally extended bent portion of the inner electrode and to then twist the entire surgical tool to ensure that the outer electrode makes the necessary contact so that the tissue can be treated with the applied current. Since this maneuver may sometimes be difficult or unacceptable to some surgeons, improved embodiments are developed to have the structures illustrated in FIGS. 16(A)–20(C).

These new structures include a very valuable feature which can be incorporated into the form of the outer electrode for all of the embodiments disclosed earlier as well.

This feature is the provision of a slim highly distinctive and readily viewable narrow strip longitudinally along a selected portion of the outer electrode. With the use of known means for providing lighting and viewing of a lighted portion of the surgical side, e.g., by the incorporation of optical fibers and lenses in conventional cannula structures, the surgeon can then precisely orient the electrosurgical tool by viewing the clearly visible slim line. The surgeon is thus spared the stress that might otherwise result if the surgeon had to struggle to see the very distal tip of the tool while performing very precise surgery under difficult circumstances and/or during a prolonged surgical procedure.

Figure 16A:
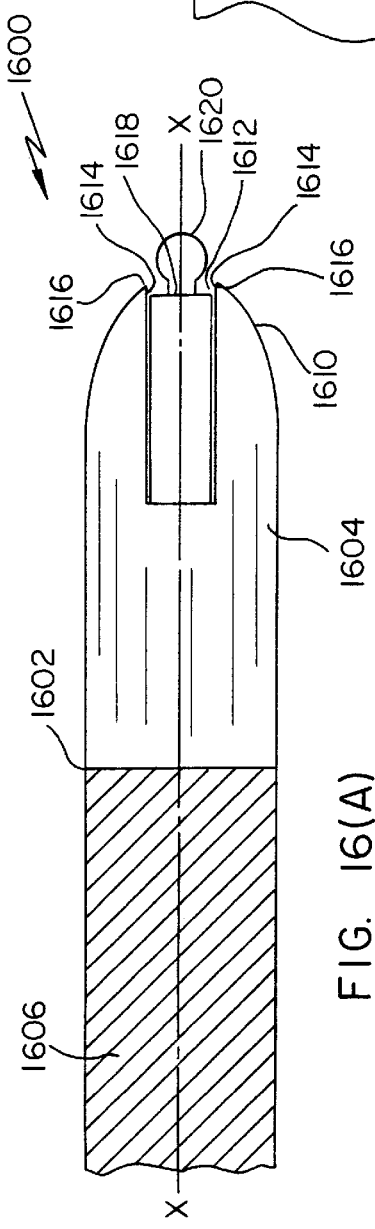
FIGS. 16(A) and 16(B) are two longitudinal diametrally opposite side views of a preferred embodiment of electrosurgical instrument as claimed herein.
Figure 16B:
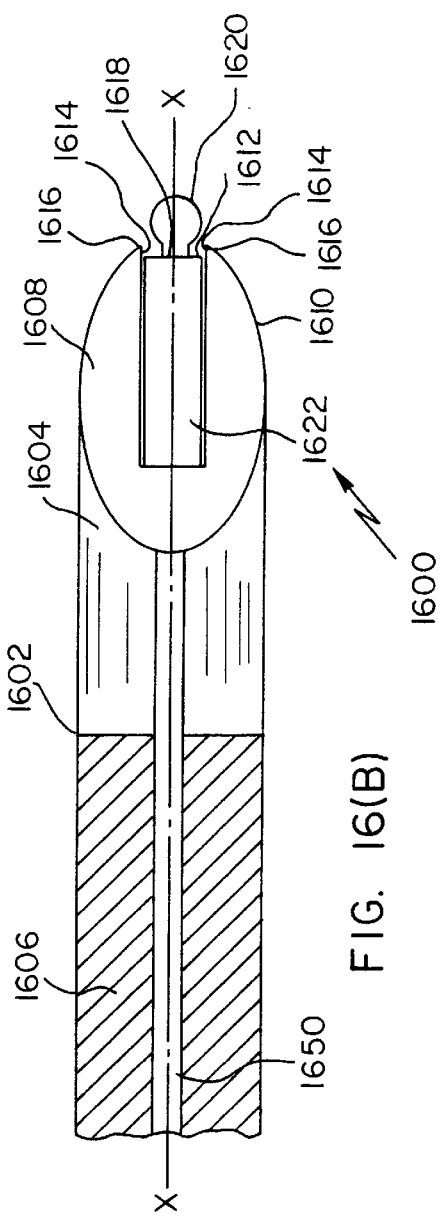

FIGS. 16(A) and 16(B) are two diametrally opposite longitudinal side views of a preferred embodiment 1600. In this embodiment, as in the others previously discussed, there is provided an elongate cylindrical outer electrode 1602 which has a distal uninsulated portion 1604 and a longer portion insulated by an outer insulating sleeve or layer 1606. The outer surface of the uninsulated portion 1604 of outer electrode 1600 is defined in part by a transverse end surface 1608 inclined at a first angle "$\alpha_1$" relative to a longitudinal axis X—X of the outer electrode, as best seen in FIGS. 18(A)–18(C). The intersection of inclined plane surface 1608 and the cylindrical outer surface 1604 of the uninsulated portion defines an elliptical edge 1610.

In the preferred embodiment 1600, an axially oriented cutout 1612 is cut or formed in any known manner inwardly from the forwardmost portion of the elliptical edge 1610, preferably across a substantial length but not all of the major diameter of the elliptical shape of inclined surface 1608. It is preferred that this cutout 1612 (which has the form of an open-ended slot) be defined between two planes 1614, 1614 each of which is parallel the longitudinal axis X—X and perpendicular to the inclined surface 1608.

The intersection of parallel planes 1614, 1614 with the elliptical edge 1610, at the very front of outer electrode 1600 defines two corners 1616, 1616 which represent the forward opening of cutout 1612.

Coaxially inside outer electrode 1600 is provided an inner electrode 1618 ending in a rounded bulbous end 1620. Inner electrode 1618 has most of its length within an insulating sleeve 1622, so that only a distal end portion is effectively uninsulated and available for electrical contact with selected tissue.

As will be readily appreciated from FIG. 16(B), the parallel planes 1614, 1614 are spaced apart by a distance sufficient to accommodate closely therein the insulating sleeve 1622 of inner electrode 1618. It should be understood that although the term "insulating sleeve" is used in referring to element 1622, this is not meant to restrict the actual structure of this element to a distinct sleeve, i.e., the disclosed invention would function even if the substantial portion of inner electrode 1618 which is to be insulated were provided with a coating or layer of an electrically insulating material suitable for surgical applications. Such an electrically insulating layer could be applied to the outer surface of the body of inner electrode 1618 by sputtering, chemical vapor deposition, or any other known technique. The important thing is that a selected length of the distal generally cylindrical end portion and a rounded bulbous end of the inner electrode be allowed to project from the terminal end of the insulating sleeve or layer 1622 very close to but electrically insulated from the uninsulated outer surface of outer electrode 1602.

FIG. 16(B) also shows another highly advantageous aspect of this embodiment, i.e., the formation of a slim strip 1650 extending longitudinally along the outer surface of outer electrode 1602, preferably contiguously across both insulating sleeve 1606 and the uninsulated generally cylindrical portion of the surface of distal end portion 1604 to end at the intersection of insulated cylindrical surface 1604 with the inclined surface 1608. As will be readily understood by persons of ordinary skill in the art, the surgeon can view stripe 1650 and use it as an orientation guide to orient the uninsulated tissue-contactable surface of the cooperating electrodes.

Stripe 1650 may be generated by the application of any suitable readily viewable material, and preferably may be no more than 1 mm wide and of a highly reflective white color. It may be applied by any known technique which will ensure permanent adhesion of the selected material of strip 1650 to both the insulation sleeve 1606 and the material of outer electrode 1602. The exact manner in which such a stripe is produced is not critical, and what is important is its presence and orientation relative to the inner and outer electrodes.

Figure 17A:
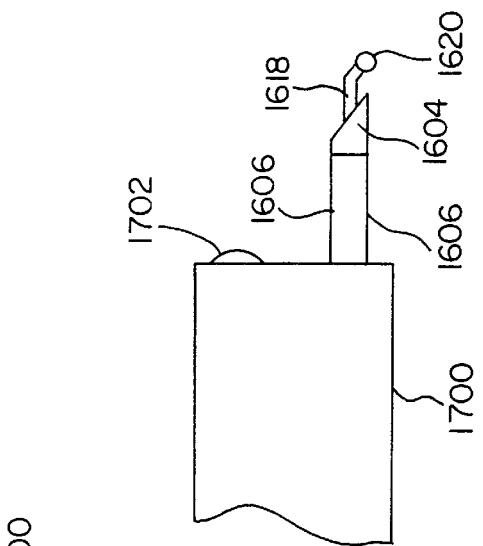
FIG. 17(A) is a partial side view at the distal end of a cannula, with the distal end portion of the electrosurgical instrument per FIGS. 16(A) and 16(B) projecting therethrough as it may be disposed during use.

Reference to FIG. 17(A) shows a distal end of a cannula 1700 provided at an end surface with a lens 1702 in a known arrangement by which optic fibers (not shown for simplicity) are employed to convey light projected from lens 1702 generally forwardly along the direction of cannula 1700. Cooperating optic fibers (also not shown) are provided within the cannula 1700 to receive reflected light to permit viewing thereby of objects and tissue within a defined field of vision.

Figure 17B:
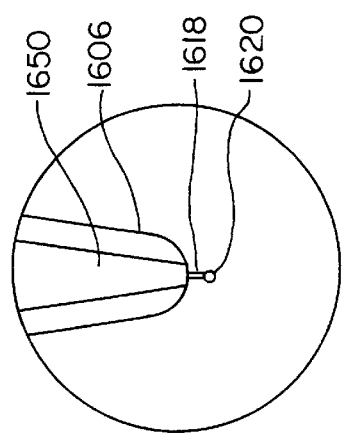
FIG. 17(B) is a schematic drawing to indicate how a surgeon employing the apparatus per FIG. 17(A) may view a white stripe provided longitudinally on an upper surface portion of the electrosurgical instrument (per FIG. 16(B)) as deployed during use.

FIG. 17(B) is a schematic view of what a surgeon may see on known apparatus displaying reflected light received through lens 1702 from objects and tissue in the field of vision. As will be appreciated, the surgeon performing a complicated procedure, e.g., in a laparoscopic surgery or in neurosurgery, would be viewing a conventional display monitor and, with the structure just described, should therefore be able to see the distal end of stripe 1650 and thereby be fully aware of the orientation of inner electrode 1618 and the simultaneous orientation of corners 1616, 1616 of cutout 1612.

FIGS. 18(A), 18(B) and 18(C) are longitudinal cross-sectional views to explain possible geometrical variations of the embodiment per FIGS. 16(A)–16(B). These variations differ from each other in the relative cooperative dispositions of the uninsulated portions of the inner and outer electrodes 1618, 1602 relative to each other. Each of these variations affects the manner in which the desired simultaneous contact with the tissue to be operated on is effected by individual surface contact by the respective electrodes. Depending on the particular geometry, more or less area of each of the electrodes makes contact with the tissue at the surgical site and, perhaps more important, each geometrical variant influences the location and amount of contacted tissue through which the applied high frequency current will pass between the contacting surfaces of the electrodes during operational use of the device.

For ease of reference and comparison among the different variants, it may be helpful to visualize an imaginary line passed through the corners 1616, 1616 at the very inlet of the cutout 1612 as one reference line from which distances "$x_a$", "$x_b$", "$x_c$", etc. may be measured along the plane of inclined surface 1608 as shown in FIGS. 18(A)–18(C). It is also helpful to consider a distance, e.g., "$y_a$", "$y_b$", "$y_c$", etc., in a direction perpendicular to the plane of inclined surface 1608, also as shown in FIGS. 18(A)–18(C). These terms of reference are employed in the discussion which follows.

Referring to the variant per FIG. 18(A), it becomes clear that at least a portion of insulating sleeve 1622 which surrounds the inner electrode 1618 lies within the width of cutout 1612 defined between the parallel surfaces 1614, 1614. However, in this variant, that portion of the inner electrode which lies distally of the bend or elbow at 1850 has a central axis Y—Y which is inclined to the axis X—X at an angle "$\alpha_2$" which may or may not be equal to the angle "$\alpha_1$" which inclined plane surface 1608 makes with the same axis X—X. In this particular variant, with the rounded bulbous end 1620 of inner electrode 1618 considered as a virtual sphere, a distance "$x_a$" is defined between the leading edge corners 1616, 1616 and the center of the rounded bulbous end 1620 of the inner electrode. At the same time, there is a distance "$y_a$" defined between the plane surface 1608 and the center of the rounded bulbous end 1620 of the inner electrode. With this particular configuration, with simultaneous contact between the surface of the relatively large uninsulated distal end of the outer electrode and the relatively small tissue-contactable uninsulated distal surface of the inner electrode, a high frequency current passed between the two electrodes will result in a much higher current density at the inner electrode than at the outer electrode. This very high current density in the tissue contacting the inner electrode will cause intense local heating of the contacted tissue. Local heating by the surgeon-controlled applied current may be high enough to cause an incision or may be made just enough to coagulate any fluid leakage at the incision site.

It should be appreciated that the current flow between the two tissue-contacting electrode surfaces will not pass through tissue located even a small distance away from the operational site but will be limited to pass substantially through only that portion of the tissue which lies between the above-discussed imaginary line joining lead corners 1616, 1616 and the tissue-contacting relatively small surface of the uninsulated end portion of inner electrode 1618. Note, however, that among the three variants illustrated in FIGS. 18(A), 18(B) and 18(C), the distance "$x_a$" is the largest (see FIG. 18(A)). Such an embodiment, therefore, should permit somewhat deeper cuts to be made than may be possible with the embodiment of, for example, FIG. 18(C).

FIG. 18(B) corresponds to the embodiment illustrated in FIGS. 16(A) and 16(B) more closely than do the two variants respectively illustrated in FIGS. 18(A) and 18(C). In the variant of FIG. 18(B), the distance "$x_b$" is quite small and the amount of tissue-contactable available surface area of the uninsulated distal end portion of inner electrode 1618 is only a fraction of the curved surface of the rounded bulbous end 1620 thereof. In this case, with the distance "$x_b$" being relatively small and "$y_c$" virtually zero, only a relatively small amount of tissue will experience the through-flow of high frequency current. Such an embodiment, therefore, may be particularly useful for very fine detailed incisions. It should be remembered that the amount of current can be controlled with the use of any known control means and as generally described earlier, so that it should be quite easy for the surgeon to selectively pass a relatively large or small controlled current through a relatively small amount of tissue between the uninsulated tissue-contacting surfaces of the inner and outer electrodes to perform correspondingly different surgical procedures with the single tool.

The variant shown in FIG. 18(C) has the body of the inner electrode retracted even further along axis X—X, to the point that the junction or elbow 1850 (at which the axes X—X and Y—Y intersect), is located at about the end of the cutout 1612. In this particular configuration, the distance "$x_c$" is larger than the distance "$x_b$" in the variant of FIG. 18(B) but is inwardly of the location of lead corners 1616, 1616 and, furthermore, the distance "$y_c$" is measurable below the inclined plane 1608. The curved surface of rounded bulbous end 1620 is, in effect, bracketed on both sides by the uninsulated tissue-contactable surface of the outer electrode. Thus, with the high frequency current controlled to be at a relatively low value, this embodiment might be particularly useful for sealing-off incised blood vessels and/or to coagulate body fluids.

The outer electrode 1602 does not have to be made of a single piece of metal. In fact, with microengineering techniques, it may be more convenient to make the main body of the outer electrode from a thin-walled metal tubing 1802 enveloped in an outer insulation sleeve or layer 1606 and, at the distal open end of the tubular length 1802 to press in a reduced diameter portion 1806 of a metal end element 1804. Any known electrically conductive material 1808 may be employed to ensure good electrical contact between the inner cylindrical surface of tubular length 1802 and the outer cylindrical surface of the reduced portion 1806, as generally indicated in FIG. 18(B). With this arrangement, the inclined plane face 1608 may be machined or otherwise formed and cutout 1612 also machined or otherwise formed before the union between tubular length 1802 and reduced portion 1806 is obtained. These are mere design choices, and the key is that only a limited amount of the distal end portion of the outer electrode is kept uninsulated and, at the same time, the inner electrode is positioned coaxially with the outer electrode with only a relatively small uninsulated distal end area electively disposed to make tissue contact during use.

Persons of ordinary skill in the art can fairly be expected to consider other obvious variations of relationships between the inner and outer electrodes.

Additional exemplary variants are illustrated in longitudinal cross-sectional view in FIGS. 19(A)–19(C) and in corresponding respective end views 20(A)–20(C). In each of these, the axis Y—Y lies in the plane of inclined surface 1608, but these variants differ from each other in the length of the insulation sleeve 1622 and the length of the inner electrode 1618 distally projected therefrom along and within the cutout 1612. For each of these variants, if the rounded bulbous end portion 1620 of the inner electrode is considered as a sphere, the center of this sphere always lies in the plane of inclined plane surface 1608, although the distance relative to the imaginary line joining lead corners 1616, 1616 varies and is various identified by the symbols "$l_a$", "$l_b$" and "$l_c$" as shown in FIGS. 19(A)–19(C).

In the variant shown in FIG. 19(A), if the surgeon using the surgical tool applies only the forwardmost part of each of the electrodes to tissue, the applied current will be restrained to pass only through tissue bracketed between lead corners 1616, 1616 (best seen in FIG. 20(A)).

With the variant shown in FIG. 19(B), the performance will be very similar to that realizable with the variant shown in 18(B) if the distances "$x_b$" in each case are the same, since the straight cylindrical portion of the insulated exposed distal end of inner electrode 1618 is located where it will not make any substantial contact with tissue, such contact being limited to the curved portion of the rounded bulbous end 1622 and the bracketing portions of the surface of outer electrode 1602.

Note, however, that the variant per FIGS. 19(C) and 20(C) has a relatively long expanse of the cylindrical distal end portion of inner electrode 1618, corresponding to a length "$l_c$" measurable between the end of insulating sleeve 1622 and the center of rounded bulbous end 1620. With this variant, the tissue contacted by that portion of the inner electrode which projects forwardly of the outer electrode can be virtually "hooked" to make relatively deeper incisions by passing high frequency current through tissue between the lead corners 1616, 1616 and the tissue contacting surface of the inner electrode.

As persons of ordinary skill in the art will appreciate from the above, seemingly minor variations in the geometry of the "cutout" embodiment, in which the outer electrode is slotted at its end, provide an electrosurgical tool of great versatility. All surgical equipment tends to be expensive, and electrosurgical equipment perhaps more so than other types. Also, while conventional incision tools such as scalpels can be readily sterilized and reused, this is not always easy or possible with electrosurgical tools due to their relatively smaller-sized components and relative fragility. It is, therefore, very important for manufacturers of such tools, the surgeons who use them, and the patients and/or insurance companies who pay for them, that economies of scale and all other simplifying design considerations be fully taken into account.

As noted above, relatively minor variations in the location of the substantially longitudinal portion of the inner electrode relative to the coaxial outer electrode permits the same basic elements to be put in cooperative relationships which permit a wide range of surgical performance of the resulting tool. The manufacturer, therefore, needs to produce only a relatively few elements in large numbers and to then assemble them in selected dispositions within the surgical tool to provide the selected performance. This should permit realization of economies of scale, and allow simplicity of manufacturing techniques and quality control superior to those available with other electrosurgical tools known in the art. The disposition of the distal end portion of the inner electrode within a slot formed in the outer electrode, permit the surgeon to avoid having to use a hooking and twisting maneuver. By simply selecting the appropriate variant for the end portion of the surgical tool, even a very tired surgeon involved in a long surgical operation can align the surgical tool easily by viewing the distinctive stripe formed on the visible surface of the outer electrode to precisely incise, coagulate or cauterize very specific portions of the tissue at the surgical site.

In summary, it is considered that the preferred embodiment with the "cutout" as disclosed herein provides a highly versatile electrosurgical tool which can be manufactured relatively inexpensively, used comfortably by surgeons, and through its different variants makes possible a variety of surgical operations.

Although in the above-discussed drawing figures the angles "$\alpha_1$" and "$\alpha_2$" are both shown for convenience as equal, this is not intended to be limiting in any manner. Thus, as persons of ordinary skill in the art will readily appreciate, by making "$\alpha_2$" smaller than "$\alpha_1$" other geometric variations can be realized and may prove to be of particular value for specific types of surgical operations. A surgeon probably can adjust "$\alpha_2$" at will to suit a particular need. Since it would be impossible to provide an exhaustive description of all such possible variations, and since the choice of the angular inclinations is only one of many factors, including the distances identified by the letters "x", "y", and "l", a more detailed description is not considered necessary. Persons of ordinary skill in the art, e.g., surgeons and electrosurgical tool designers, can make detailed selections of these parameters as needed.

A surgical maneuver which may be of potential interest to oncologists who need to obtain small tissue samples for specific analysis, may be to carefully control the applied electrical current with the variant of FIGS. 19(A) and 19(B), and to rotate the surgical tool substantially about the axis Y—Y so that a circular incision may be defined by the lead points 1616, 1616 and a small tissue sample of circular shape incised thereby. Then, using conventional tools through the same or another cannula the surgeon may pick up that small incised portion of the tissue for removal and testing. It is believed that once such an electrosurgical tool is made generally available to surgeons other possibilities will be considered and many useful surgical techniques developed with obvious modifications of the invention disclosed and claimed herein.

Preferred ranges of values for various geometric parameters discussed herein are as follows:

$x_i$ (where i corresponds to a, b, c, etc.): 0–1.5 cm.

$y_i$ (where i corresponds to a, b, c, etc.): 0–0.5 cm.

$l_i$ (where i corresponds to a, b, c, etc.): 0–1.5 cm.

$\alpha_1$ or $\alpha_2$: 25°–50°.

In this disclosure, there are shown and described only the preferred embodiments of the invention, but, as aforementioned, it is to be understood that the invention is capable of use in various other combinations and environments and is capable of changes or modifications within the scope of the inventive concept as expressed herein.

Therefore, although the present invention has been described and illustrated in detail, it should be clearly understood that the same is by way of illustration and example only and is not to be taken by way of limitation, the spirit and scope of the present invention being limited only by the terms of the appended claims.

What is claimed is:

1. An electrosurgical instrument for performing surgical operations on tissue, comprising:

an elongate tubular outer electrode covered with outer insulating sleeve which leaves a distal end portion of the outer electrode uninsulated;

an elongate inner electrode, located coaxially about a common axis within the outer electrode;

an inner insulating sleeve surrounding the inner electrode to electrically insulate the inner electrode from the outer electrode, a distal end of the inner insulating sleeve being located so that a distal uninsulated end portion of the inner electrode extends to a first predetermined length from the distal end of the inner insulating sleeve to enable simultaneous electrical contact by the distal uninsulated end portions of both the inner and outer electrodes with the tissue to be operated on; and means for providing an alternating electrical voltage difference at a controlled frequency between the inner and outer electrodes, wherein the distal end portion of the outer electrode has a transverse end surface inclined at a first angle relative to a common axis of the inner and outer electrodes, the transverse end surface and an outer peripheral surface of the outer electrode intersect at an acute angle to form a leading edge of the outer electrode, a leading edge portion of the outer electrode has an axially oriented cutout extending inwardly from the leading edge, and at least a distal end portion of the insulating sleeve is located within the cutout.

2. The electrosurgical instrument according to claim 1, wherein:

the distal uninsulated end portion of the inner electrode has a rounded bulbous end and has a total first surface area which is less than a second surface area of the distal uninsulated end portion of the outer electrode.

3. The electrosurgical instrument according to claim 2, wherein:

a ratio of the total first surface area to the second surface area is less than 1:2.

4. The electrosurgical instrument according to claim 1, wherein:

at least the distal uninsulated end portion of the inner electrode is inclined at a second angle relative to the common axis and has a rounded bulbous end.

5. The electrosurgical instrument according to claim 4, wherein:

the distal uninsulated inclined and portion of the inner electrode is oriented substantially parallel to the transverse end surface.

6. The electrosurgical instrument according to claim 4, wherein:

the second angle is approximately 30°.

7. The electrosurgical instrument according to claim 5, wherein:

at least a part of the rounded bulbous end of the inclined end portion of the inner electrode extends radially outward of the outer peripheral surface of the outer electrode.

8. The electrosurgical instrument according to claim 7, wherein:

the distal uninsulated end portion of the inner electrode, including the rounded bulbous end thereof, has a total first surface area which is less than a second surface area of the distal uninsulated end portion of the outer electrode.

9. The electrosurgical instrument according to claim 8, wherein:

a ratio of the total first surface area to the second surface area is less than 1:2.

10. The electrosurgical instrument according to claim 1, wherein:

a width of the cutout is defined between two parallel surfaces each perpendicular to the transverse end surface and parallel to the common axis; and the two parallel surfaces intersect the forward edge to define two forward corners bounding a front of the cutout.

11. The electrosurgical instrument according to claim 2, wherein:

a width of the cutout is defined between two parallel surfaces each perpendicular to the transverse end surface and parallel to the common axis; and the two parallel surfaces intersect the forward edge to define two forward corners bounding a front of the cutout.

12. The electrosurgical instrument according to claim 11, wherein:

the distal uninsulated end portion of the second electrode is inclined at a second angle to the common axis.

13. The electrosurgical instrument according to claim 12, wherein:

the first and second angles are equal.

14. The electrosurgical instrument according to claim 13, wherein:

the rounded bulbous end of the inner electrode is substantially spherically shaped and has a diameter defined about a substantially central point located at a first predetermined distance relative to the two forward corners in a direction along the transverse end surface; and the first predetermined distance is in a range 0–1.5 cm.

15. The electrosurgical instrument according to claim 14, wherein:

said substantially central point is located at a second predetermined distance from the transverse end surface in a direction perpendicular thereto, and the second predetermined distance is in a range 0–0.5 cm.

16. The electrosurgical instrument according to claim 1, further comprising:

means for lighting and viewing at least the uninsulated portions of the inner and outer electrodes for viewing contacting of tissue thereby.

17. The electrosurgical instrument according to claim 16, wherein:

said lighting and viewing means comprises a distinctively visible line provided longitudinally of an outer surface of the outer electrode at least to an intersection thereof with the transverse end surface, whereby the visible line is both lighted and rendered viewable to thereby enable the surgeon to selectively orient the uninsulated portions of the inner and outer electrodes.

18. A method of performing surgical operations including incisions, cauterizations and coagulations of a tissue, comprising the steps of:

providing an elongate tubular outer electrode covered with an outer insulating sleeve which leaves a distal end portion of the outer electrode uninsulated;

providing an elongate inner electrode located coaxially within the outer electrode and an inner insulating sleeve surrounding the inner electrode to electrically insulate the inner electrode from the outer electrode, a distal end of the inner insulating sleeve being located such that a distal uninsulated end portion of the inner electrode extends to a first predetermined length from the distal end of the inner insulating sleeve and has a rounded bulbous end to enable simultaneous electrical contact by the distal uninsulated end portions of both the inner and outer electrodes with the tissue to be operated on, wherein the distal end portion of the outer electrode has a transverse end surface inclined at a first angle relative to a common axis of the inner and outer electrodes, the transverse end surface and an outer peripheral surface of the outer electrode intersect at an acute angle to form a leading edge portion of the outer electrode, and a leading edge portion of the outer electrode has an axially oriented cutout extending inwardly of the leading edge, and at least a distal end portion of the insulating sleeve is located within the cutout;

providing an alternating electrical voltage difference at a controlled frequency between the inner and outer electrodes; and contacting the rounded bulbous end of the inner electrode and the distal uninsulated end portion of the outer electrode simultaneously to the tissue to be operated on, to thereby cause a high frequency, high density, current to flow substantially only through that portion of the contacted tissue which lies between tissue-contacting surfaces of the inner and outer electrodes.

19. The method according to claim 18, wherein:

the alternating voltage difference is provided so as to have a continuous waveform at a selected single frequency, to thereby enable incision of the contacted tissue between the applied inner and outer electrodes.

20. The method according to claim 18, wherein:

the alternating voltage difference is provided so as to have a periodically damped waveform, to thereby enable a user to selective cauterize and coagulate of the contacted tissue and any bodily fluids present between the tissue contacting inner and outer electrodes.

21. The method according to claim 18, comprising the further steps of:

providing a distinctively visible line longitudinally of an outer surface of the outer electrode at least to an intersection thereof with the transverse end surface;

providing lighting of said visible line, and viewing the lighted visible line.

22. The method according to claim 18, wherein:

the distal uninsulated end portion of the inner electrode, including the rounded bulbous end thereof, has a total first surface area which is less than a second surface area of the distal uninsulated end portion of the outer electrode; and the step of contacting the rounded bulbous end of the inner electrode and the distal end portion of the outer electrode simultaneously to the tissue includes a step of hooking a portion of the contacted tissue with the rounded bulbous end of the inner electrode.

23. The method according to claim 18, wherein:

the alternating voltage difference is provided so as to have a continuous waveform at a selected single frequency, to thereby enable incision of the contacted tissue between the applied inner and outer electrodes.

24. The method according to claim 18, wherein:

the alternating voltage difference is provided so as to have a periodically damped waveform, to thereby enable selective cauterization and coagulation of the contacted tissue and any bodily fluids present between the applied inner and outer electrodes.

25. The method according to claim 18, comprising the further step of:

providing known viewing means to enable the user to view a region of the patient's body which includes the tissue being operated on, wherein the step of contacting the rounded bulbous end of the inner electrode and the distal end portion of the outer electrode simultaneously to the tissue includes a step of hooking a portion of the contacted tissue with the rounded bulbous end of the inner electrode, and wherein the step of hooking tissue is performed so that the hooked tissue is positioned in a field of view of the user before and during performance of an operation on the hooked tissue.

26. The method according to claim 19, wherein:

the leading edge and the cutout define two forward corners of the uninsulated end portion of the outer electrode, and the step of contacting the uninsulated end portions of the inner and outer electrodes comprises rotating both such that as the current flows through tissue therebetween a circular plug of tissue is incised.

* * * * *